United States Patent
Min et al.

(10) Patent No.: US 9,074,235 B2
(45) Date of Patent: Jul. 7, 2015

(54) METHOD FOR EVALUATING THE IMPROVEMENT OF SKIN ELASTICITY USING A MIMETIC DERMIS

(75) Inventors: Dae Jin Min, Yongin-si (KR); Yong Joo Na, Yongin-si (KR); Soon Ae An, Yongin-si (KR); Hyae Kyoung Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 13/881,859

(22) PCT Filed: Oct. 21, 2011

(86) PCT No.: PCT/KR2011/007878
§ 371 (c)(1),
(2), (4) Date: Apr. 26, 2013

(87) PCT Pub. No.: WO2012/057473
PCT Pub. Date: May 3, 2012

(65) Prior Publication Data
US 2013/0217062 A1   Aug. 22, 2013

(30) Foreign Application Priority Data
Oct. 29, 2010  (KR) .......... 10-2010-0107001

(51) Int. Cl.
  C12Q 1/08   (2006.01)
  C12Q 1/02   (2006.01)
  C12N 5/071  (2010.01)
  G01N 33/50  (2006.01)

(52) U.S. Cl.
  CPC .............. *C12Q 1/025* (2013.01); *C12N 5/0698* (2013.01); *G01N 33/5044* (2013.01)

(58) Field of Classification Search
  None
  See application file for complete search history.

(56) References Cited

FOREIGN PATENT DOCUMENTS

JP   2009-219491   10/2009

OTHER PUBLICATIONS

Pageon et al., Exp. Geron., 43:584-588 (2008).*
Pena et al., J. Biomed. Optics, 15(5):1-7 (2010).*
Corstjens et al., Exp. Geron., 43:663-667 (2008).*
Mio et al., in Vitro Cell Dev. Biol. An., 32:427-433 (1996).*
Ngo et al., Meth. Mol. Biol., 341 (2006).*
Pageon, Path. Biol., 58:226-231 (2010).*
Pageon et al. Eur. J. Dermatol., 17(1):12-20 (2007).*
Palmiero et al., Acta Biomater., 6:2548-2553 (2010).*
Vernon et al., In Vitro Cell Dev. Biol. An., 38:97-101 (2002).*
Vernon et al (In Vitro Cell. Dev. Biol., 38:97-101 (2002).*
Hunter et al., Am. J. Physiol., 299(1):C21-C32 (2010).*
Marenzana et al., Tiss. Eng., 8(3):409-418 (2002).*
NUNC Cell Culture Inserts (2008).*
Asselineau et al., Textbook of Aging Skin, M. A. Farage, K. W. Miller, H. I. Maibach (eds.):461-475 (2010).*
International Search Report for PCT/KR2011/007878 dated May 24, 2012.
Written Opinion for PCT/KR2011/007878 dated May 24, 2012.

* cited by examiner

*Primary Examiner* — Blaine Lankford
*Assistant Examiner* — Thomas J Visone
(74) *Attorney, Agent, or Firm* — Nixon & Vanderhye P.C.

(57) ABSTRACT

The present invention relates to a method for evaluating the improvement of skin elasticity by preparing a mimetic dermis having a structure similar to that of the real dermis, and providing a three-dimensional visualization of the differences in the degree of transformation of the mimetic dermis.

16 Claims, 2 Drawing Sheets

1) Conventional collagen gel contraction assay

2) Evaluation of the improvement of skin elasticity using a mimetic dermis

METHOD FOR EVALUATING THE IMPROVEMENT OF SKIN ELASTICITY USING A MIMETIC DERMIS

This application is the U.S. national phase of International Application No. PCT/KR2011/007878 filed 21 Oct. 2011 which designated the U.S. and claims priority to KR Patent Application No. 10-2010-0107001 filed 29 Oct. 2010, the entire contents of each of which are hereby incorporated by reference.

TECHNICAL FIELD

The present invention relates to a method of evaluating improvement in skin elasticity by preparing three-dimensional dermal mimics similar to actual dermis and measuring the difference in deformation between the dermal mimics.

BACKGROUND ART

Collagen and elastin in the dermis of the skin are the major components of the dermis, which determine the tensile strength of the skin. Collagen and fibroblasts interact with each other to exhibit high elasticity which keeps the skin tight and elastic. As aging continues, fibroblasts are more inactive, or the quality of collagen is reduced or the interaction between fibroblasts and collagen is lessened, and thus the skin loses elasticity, causing wrinkles.

Because the biggest factors that determine skin elasticity are the interaction and binding force between dermal collagen and fibroblasts, the interaction between collagen and fibroblasts was measured using a collagen gel contraction assay (Experimental Dermatology, 17, 788-789) in the prior art. Specifically, skin elasticity was evaluated by mixing fibroblasts with collagen to make gels, culturing the gels in general culture dishes, comparing the degree of contraction between the gels to determine the change in interaction between collagen and fibroblasts caused by a material, and calculating the surface area of each of the gels using digital images (photographs).

However, the above method has a disadvantage in that, because it shows two-dimensional results, it cannot visually show a three-dimensional change which can occur in the actual skin.

DISCLOSURE

Technical Problem

The present inventors have found that a change which can occur in the actual skin can be predicted by preparing a dermal mimic in a three-dimensional form using a culture insert, treating the dermal mimic with a material, and then observing the degree of the structural breakdown of the dermal mimic, thereby completing the present invention.

It is an object of the present invention to provide a method capable of evaluating a skin elasticity-improving effect in a three-dimensional manner.

Technical Solution

In order to accomplish the above object, the present invention provides a method for evaluating improvement in skin elasticity, the method comprising the steps of: a) preparing a glycated collagen control group by reaction of collagen with sugar, and a glycated collagen test group by reaction of collagen and sugar with a candidate whose skin elasticity-improving effect is to be evaluated, and mixing fibroblasts with each of the control group and the test group to make gels; b) constructing a three-dimensional shape using a culture insert; c) placing and culturing each of the gels of the control group and the test group in the culture insert of step b) to prepare dermal mimics; d) obtaining three-dimensional images of the shape of the prepared mimics; and e) evaluating a change in elasticity from the images of step d).

The present invention also provides a method for screening a cosmetic material, which improves skin elasticity, using the above method for evaluating improvement in skin elasticity.

Advantageous Effects

According to the present invention, when the degree of the breakdown of a dermal mimic, which is caused by treatment with a material, is evaluated by a three-dimensional image, the changes in binding force and interaction between fibroblasts and collagen fiber caused by treatment with the material can be observed, and the changes make it possible to predict changes which can occur in the actual skin, and thus phenomena such as a decrease in skin elasticity, skin sagging and the like can be visually shown. In addition, the use of the evaluation method of the present invention can easily screen a product capable of improving skin elasticity.

BEST MODE

The present invention is directed to a method which can visually express the improvement in skin elasticity, provided by a cosmetic product, by three-dimensionally showing a change in skin elasticity using dermal mimics.

The method for evaluating improvement in skin elasticity using dermal mimics according to the present invention comprises the steps of: a) preparing a glycated collagen control group by reaction of collagen with sugar, and a glycated collagen test group by reaction of collagen and sugar with a candidate whose skin elasticity-improving effect is to be evaluated, and mixing fibroblasts with each of the control group and the test group to make gels; b) constructing a three-dimensional shape using a culture insert; c) placing and culturing each of the gels of the control group and the test group in the culture insert of step b) to prepare dermal mimics; d) obtaining three-dimensional images of the shape of the prepared mimics; and e) evaluating a change in elasticity from the images of step d).

In a collagen gel contraction assay which is a conventional evaluation method, fibroblasts are mixed with collagen to make gels which are then cultured in general culture dishes to prepare collagen gels, and the collagen gels float in media during the preparation period. In comparison with this, the evaluation method according to the present invention differs in that a three-dimensional shape is constructed using a culture insert and a collagen gel is placed and cultured in the culture insert in place of the general culture dish. During the culture process, dermal remodeling by fibroblasts occurs. As used herein, the term "dermal remodeling" refers to a process in which fibroblasts bind to collagen fibers to regulate the arrangement of the collagen fibers to thereby structurally stabilize the dermal mimic.

Figure 1:
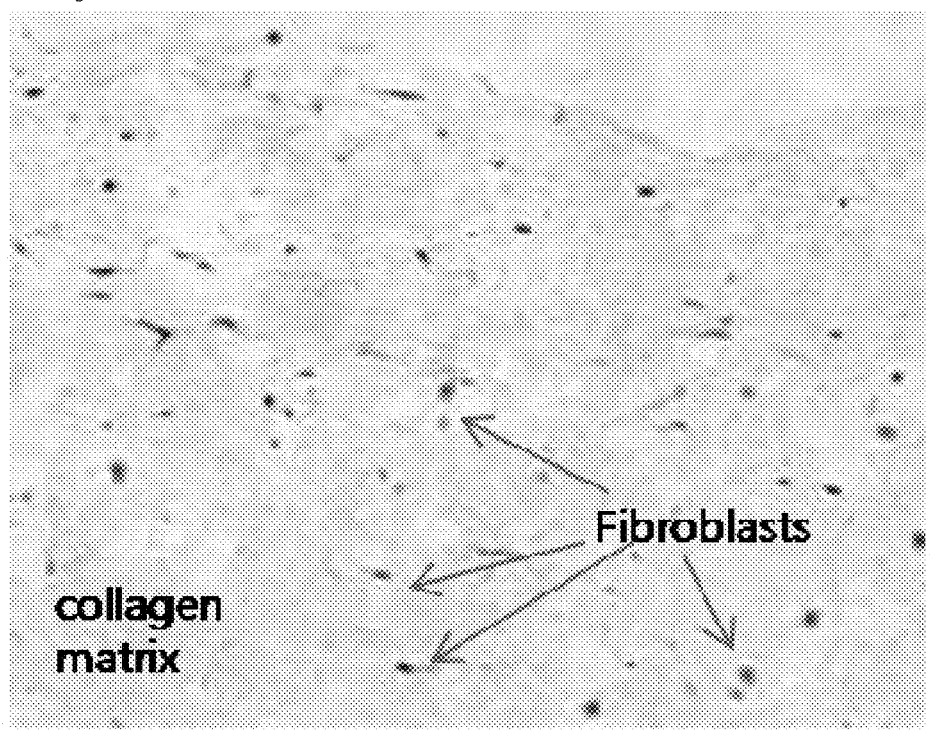
FIG. 1 is an HE staining image showing the cross-section of a dermal mimic according to the present invention.

FIG. 1 shows an HE (hematoxylin-eosin) staining image of the cross-section of the dermal mimic prepared as described above. As can be seen in FIG. 1, in the dermal mimic of the present invention, fibroblasts form a network in a collagen matrix by dermal remodeling, like an actual dermal layer, suggesting that the dermal mimic of the present invention is structurally very similar to actual dermis.

To prepare a dermal mimic according to the present invention, collagen is reacted with sugar to make a glycated collagen gel. As skin aging continues, collagen glycation occurs to reduce the binding between collagen and fibroblasts to thereby reduce skin elasticity and cause skin sagging. For this reason, in the present invention, collagen glycation which occurs in the actual skin is induced in order to prepare a dermal mimic having reduced elasticity. In the case of glycated collagen, dermal remodeling does not easily occur because of sugar attached to collagen fibers, and a dermal mimic constructed using glycated collage is structurally unstable. The kind of sugar that is used to induce collagen glycation is not specifically limited, but ribose is preferably used.

In the present invention, the skin elasticity-improving effect of a candidate is evaluated by allowing the candidate together with sugar to react with collagen and evaluating the ability of the candidate to inhibit collagen glycation. The conventional collagen contraction assay provides the two-dimensional results of collagen gel, so that the degree of contraction of the collagen gel is determined based on a change in the surface area of the gel. However, the inventive evaluation method that uses the dermal mimic provides three-dimensional results, so that the degree of structural breakdown of the dermal mimic can be determined based on a change in the volume of the dermal mimic.

According to the inventive method for a skin elasticity-improving effect using the dermal mimic, the dermal mimic is treated with a candidate predicted to have an effect on improvement in skin elasticity, so that the effect of the candidate on improvement in skin elasticity can be visually shown and evaluated, and thus materials having a skin elasticity-improving effect can be easily screened.

MODE FOR INVENTION

Hereinafter, the present invention will be described in further detail with reference to examples.

Reference Example 1

Preparation of Dermal Mimic A dermal mimic that is used in the present invention can be prepared in the following manner.

(1) 40 µl of 10× P buffer (DMEM (Dulbecco's Modified Eagle Medium (DMEM powder, Gibco, USA)), a Ham's F-12 nutrient mixture (F-12 powder, Gibco, USA), 4 ml of an antibiotic-antifungal agent (PSF, Gibco, USA) in 400 ml of sterile distilled water, 40 µl of reconstitution buffer (obtained by dissolving 2.2 g of $NaHCO_3$ and 4.77 g of HEPES in 100 ml of 0.05M NaOH, and filtering the solution) and 2 µl of 5 M NaOH were added to an Epi-tube and sufficiently mixed.

(2) 320 µl of an aqueous solution of normal collagen or an aqueous solution of glycated collagen is added to and well mixed with the mixture of step (1) and using a pipette.

(3) $10^4$ human neonatal fibroblasts (HDFn, Cascade Biologics, USA) are added to and well mixed with the solution of step (2) using a pipette so that the fibroblasts are uniformly distributed in the solution.

(4) A culture insert (12 mm, Transwell®, Corning, USA) is placed in a 12-well culture dish, and the mixture is placed in the culture insert and is allowed to react at 37° for 30 minutes so that the aqueous collagen solution is hardened.

(5) After the collagen has been completely hardened, fibroblast culture medium (M106, Cascade Biologics, USA) is added to both the inside and outside of the culture insert and incubated overnight. Then, the dermal mimic is incubated for in about one week while the medium is replaced at 3-day intervals. In this process, dermal remodeling occurs due to the interaction between the fibroblasts and the collagen fibers.

Example 1

Comparison between a Collagen Gel Contraction Assay and an Evaluation Method Employing Dermal Mimics Collagen was reacted with ribose to induce glycation of the collagen, after a collagen gel and a dermal mimic were prepared in order to evaluate the influence of collagen glycation on the skin.

Specifically, the dermal mimics were prepared according to the method of Reference Example 1, and the glycated collagen solution used in step (2) of the preparation method of Reference Example 1 was obtained by treating collagen with ribose at concentrations of 0, 62.5, 125 and 250 mM to induce collagen glycation. In addition, the ribose used was obtained by dissolving D-ribose (Sigma, USA) in water and filtering the solution through a 0.2 µm filter (Minisart® sartorious stedim biotech, Germany).

A specific method for glycation of collagen is as follows. D-ribose was added to a solution of collagen (obtained by dissolving type I collagen (Sigma, USA) in 0.1% acetic acid to a final concentration of 3 mg/ml) at specific concentrations (62.5, 125 and 250 mM) in a clean bench for preventing the contamination of collagen, and the mixture was placed in a rotation mixer rotatable at 360°, after which the mixture was allowed to react at room temperature for 3 days to induce glycation of the collagen.

After completion of the culture of the dermal mimic as described above, the dermal mimics were separated from the culture inserts using a surgical knife and placed on cell culture dishes, and then the changes in volume of the dermal mimics as a function of time were observed. Generally, the dermal mimics were observed at about 10 minutes after separation from the culture inserts, and their three-dimensional images were obtained using a DSLR camera (Canon Kiss Digital N, Canon Inc., Japan) and analyzed based on the difference in height on images between the dermal mimics.

A change in volume of a structurally stable dermal mimic is not significant, but a structurally unstable dermal mimic is broken down with time after separation from the culture insert so that the height thereof on the image is lowered and the volume thereof gradually decreases. Thus, the height of the dermal mimic on the image is proportional to the structural stability of the dermal mimic.

In addition, for comparison, a collagen gel contraction assay which is a two-dimensional method was carried out by culturing a collagen gel, obtained by mixing fibroblasts with collagen glycated with the above-described concentrations of ribose, in a general culture dish, and obtaining a digital image of the cultured collagen gel.

Figure 2:
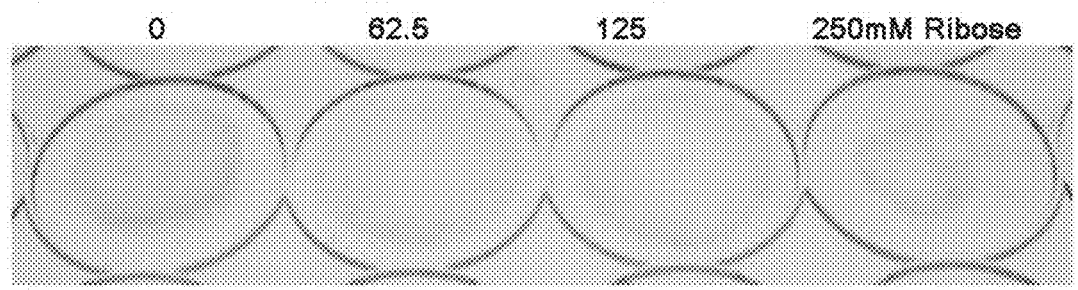
FIG. 2 shows the results obtained using each of a conventional collagen gel contraction assay and the inventive evaluation method employing dermal mimics.
Figure 2:
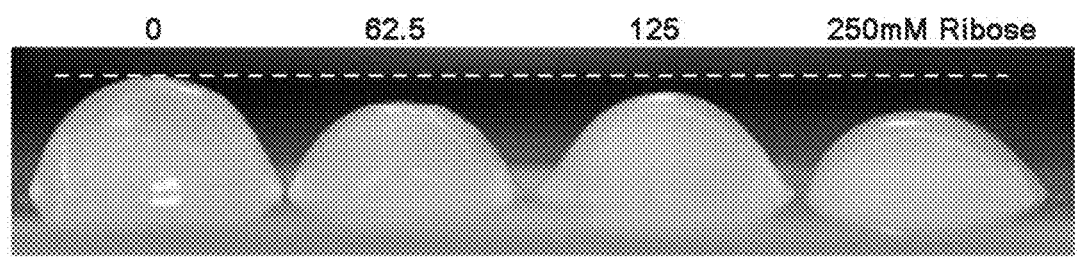

FIG. 2 shows the results obtained by the above-described two methods.

Portion 1) of FIG. 2 shows the two-dimensional results of the collagen gel contraction assay in which the collagen gel does not normally contract. As can be seen therein, the collagen gels were not contracted by ribose treatment so that they appear like as if they became wider laterally.

Portion 2) of FIG. 2 shows that the dermal mimics which weakened by collagen glycation were deformed (broken down) without maintaining their normal shapes. As can be seen therein, the method of the present invention visually shows the change in the three-dimensional structure, indicating that the dermis loses elasticity due to collagen glycation and is deformed so that the skin sags.

As can be seen in FIG. 2, the conventional gel contraction assay presents two-dimensional results, whereas the method of the present invention can visually present three-dimensional results, and thus can more effectively show changes which can occur in the actual skin.

Example 2

Evaluation of Skin Elasticity-improving Effect Using Dermal Mimics

To screen materials having an effect on improvement in skin elasticity, the dermal mimics prepared in Reference Example 1 of the present invention were used.

Specifically, in this Example, the following collagens were prepared: non-glycated collagen (normal collagen); collagen glycated by treatment with 62.5 mM of ribose; collagen glycated by treatment with 62.5 mM of ribose together with 10 ppm of tocopherol; and collagen glycated by treatment with 62.5 mM of ribose together with 1 ppm of DPHP. Herein, the ribose used was obtained by dissolving D-ribose (Sigma, USA) in water and filtering the solution through a 0.2 µm filter (Minisart® sartorious stedim biotech, Germany).

A specific method for glycation of collagen is as follows. 62.5 mM of D-ribose alone or in a combination with 10 ppm of tocopherol or 1 ppm of DPHP was added to a solution of collagen (obtained by dissolving type I collagen (Sigma, USA) in 0.1% acetic acid to a final concentration of 3 mg/ml) in a clean bench for preventing the contamination of collagen, and the mixture was placed in a rotation mixer rotatable at 360°, after which the mixture was allowed to react at room temperature for 3 days to induce glycation of the collagen.

Fibroblasts were mixed with each of the collagens prepared as described above, and each of the mixtures was placed and cultured in a culture insert (12 mm Transwell® Corning, USA) constructed to have a three-dimensional shape, thereby preparing dermal mimics.

Figure 3:
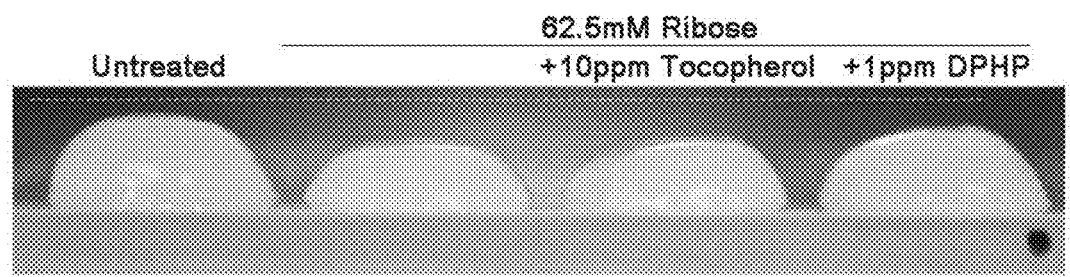
FIG. 3 shows the results of evaluating a skin elasticity-improving effect using dermal mimics according to the present invention.

After completion of the culture of the dermal mimics, the dermal mimics were separated from the culture inserts using a surgical knife and placed on cell culture dishes. The dermal mimics were observed at about 10 minutes after separation from the culture inserts, their three-dimensional images were obtained using a DSLR camera (Canon Kiss Digital N, Canon Inc., Japan) and analyzed based on the difference in height on images between the dermal mimics. FIG. 3 shows the three-dimensional images of the dermal mimics.

As can be seen in FIG. 3, the shape of the dermal mimics was broken down by treatment with ribose. However, when the dermal mimics were treated with ribose together with the conventional anti-aging material tocopherol or DPHP, breakdown of the dermal mimics was inhibited.

As described above, the use of the method of the present invention can visually and easily evaluate candidates that can increase skin elasticity by inhibiting collagen glycation caused by skin aging. In addition, the use of the method of the present invention can effectively screen materials that help increase skin elasticity.

The invention claimed is:

1. A method for quantifying improvement in skin elasticity, the method comprising the steps of:
   a) preparing (i) a glycated collagen control group by reaction of collagen with sugar without a candidate whose skin elasticity-improving effect is to be evaluated and (ii) a glycated collagen test group by reaction of collagen and sugar with the candidate, and mixing fibroblasts with each of the control group and the test group to make aqueous collagen solution;
   b) constructing three-dimensional shapes by placing each aqueous collagen solution of the control group and the test group in culture inserts to harden as gels;
   c) culturing each of the gels of the control group and the test group in their culture inserts of step b) to prepare dermal mimics;
   d) obtaining three-dimensional images with a three-dimensional imaging device of the three dimensional shapes of the prepared mimics after separation from their culture inserts; and
   e) measuring a change of at least thickness or volume of the prepared mimics from the images of step d).

2. A method for screening a cosmetic material, which improves skin elasticity, the method comprising using the steps of:
   a) preparing (i) a glycated collagen control group by reaction of collagen with sugar without candidate cosmetic materials whose skin elasticity improving effect is to be evaluated and (ii) a glycated collagen test group by reaction of collagen and sugar with the candidate, and mixing fibroblasts with each of the control group and the test group to make gels;
   b) constructing three-dimensional shapes by placing each aqueous collagen solution of the control group and the test group in culture inserts to harden as gels;
   c) culturing each of the gels of the control group and the test group in their culture inserts of step b) to prepare dermal mimics;
   d) obtaining three-dimensional images with a three-dimensional imaging device of the three dimensional shapes of the prepared mimics after separation from their culture inserts;
   e) measuring a change of at least thickness or volume of the prepared mimics from the images of step d); and
   f) selecting at least one candidate that improves skin elasticity in a dermal mimic of the test group as compared to a dermal mimic of the control group as the cosmetic material able to inhibit collagen glycation based on the measurement of step e).

3. The method according to claim 1, wherein the gels of the control group and the test group are not floated in culture medium before the dermal mimics are prepared in step b).

4. The method according to claim 1, wherein the improvement in elasticity is quantified by the difference between thicknesses of the prepared mimics without and with the candidate.

5. The method according to claim 1, wherein the improvement in elasticity is quantified by the difference between volumes of the prepared mimics without and with the candidate.

6. The method according to claim 1, wherein the three-dimensional imaging device is a digital camera.

7. The method according to claim 3, wherein the three-dimensional imaging device is a digital camera.

8. The method according to claim 4, wherein the three-dimensional imaging device is a digital camera.

9. The method according to claim 5, wherein the three-dimensional imaging device is a digital camera.

10. The method according to claim 2, wherein the gels of the control group and the test group are not floated in culture medium before the dermal mimics are prepared in step b).

11. The method according to claim 2, wherein the change of at least thickness is measured in step e).

12. The method according to claim 2, wherein the change of at least volume is measured in step e).

13. The method according to claim 2, wherein the three-dimensional imaging device is a digital camera.

14. The method according to claim 10, wherein the three-dimensional imaging device is a digital camera.

15. The method according to claim 11, wherein the three-dimensional imaging device is a digital camera.

16. The method according to claim 12, wherein the three-dimensional imaging device is a digital camera.

* * * * *